United States Patent [19]

Sevilla et al.

[11] Patent Number: 5,310,930
[45] Date of Patent: May 10, 1994

[54] BENZOFURANYLIMIDAZOLE DERIVATIVES, A PROCESS FOR THEIR PREPARATION AND THERAPEUTICAL COMPOSITIONS CONTAINING THE SAME

[75] Inventors: Jesus A. G. Sevilla, Mallorca; José J. M. Martinez, Victoria-Gasteiz; Fernando B. Fernandez, Bizkaia; Fernando A. G. Caballero, Barcelona; Angel M. Banos, Barcelona; Rosendo O. Vidal, Barcelona; Francesc P. Rodas, Barcelona, all of Spain

[73] Assignee: Societe de Conseils de Recherches et d'Applications Scientifiques (S.C.R.A.S), France

[21] Appl. No.: 995,790

[22] Filed: Dec. 23, 1992

[30] Foreign Application Priority Data

Dec. 27, 1991 [GB] United Kingdom ........... 9127430

[51] Int. Cl.⁵ ......................... C07D 405/04
[52] U.S. Cl. ......................... 548/311.4
[58] Field of Search ...................... 548/311.4

[56] References Cited

U.S. PATENT DOCUMENTS

| | | | |
|---|---|---|---|
| 3,927,023 | 12/1975 | Brown et al. | 260/309.6 |
| 4,510,149 | 4/1985 | Cozzi et al. | 548/311.4 |
| 4,950,681 | 8/1990 | Cavalla et al. | 548/311.4 |
| 4,985,440 | 1/1991 | Cozzi et al. | 514/397 |

FOREIGN PATENT DOCUMENTS

| | | |
|---|---|---|
| 0071368 | 2/1983 | European Pat. Off. . |
| 0310745 | 4/1989 | European Pat. Off. . |
| 593967 | 12/1977 | Switzerland . |

OTHER PUBLICATIONS

Chapleo, C. B. et al., "α-Adrenoreceptor Reagents. 2. Effects of Modification of the 1,4-Benzodioxan Ring System on α-Adreno-receptor Activity," J. Med. Chem. 1984, 27, 570-576.

Shridhar et al., "Benzofuran Derivatives: PartII—Synthesis & Biological Activity of Some New 2-Benzofurancarboxamidine Derivatives", Indian Journal of Chemistry, vol. 18B. Sep. 1979, pp. 254-256.

Langin et al., "Binding of [³H]Idazoxan and of Its Methoxy Derivative [³H] RX821002 in Human Fat Cells: [³H]Idazoxan but Not [³H] RX821001 Labels Additional Non-a₂-Adrenergic Binding Sties": Molecular Pharmacology, 37:876-885 (1990).

Bousquet et al., "New Concepts on the Central Regulation of Blood Pressure", The American Journal of Medicine, vol. 87, Sep. 1989, pp. 3C-10S-3C-13S.

Göthert et al., "Involvement of presynaptic imidazoline receptors in the a₂-adrenoceptor-independent inhibition of noradrenaline release by imidazoline derivatives", Arch Pharmacol (1991) 343:271-282.

S. Tanaka, "Courmarones from o-Hydroxyaldehydes and Bromomalonic Ester", J. Am. Chem. Soc. (1951) 73:872.

Jackson et al., "The effects of idazoxan and other a₂-adrenoceptor antagonists on food and water intake in the rat", Br. J. Pharmacol. (1991), 104:258-262.

Primary Examiner—Patricia L. Morris
Attorney, Agent, or Firm—Lucas & Just

[57] ABSTRACT

The invention relates to benzofuranylimidazole derivatives of the general formula (1)

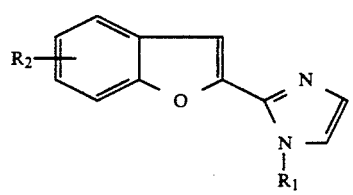

(1)

wherein $R_1$ and $R_2$ represent various radicals, to a process for their preparation and to pharmaceutical compositions containing them.

6 Claims, No Drawings

BENZOFURANYLIMIDAZOLE DERIVATIVES, A PROCESS FOR THEIR PREPARATION AND THERAPEUTICAL COMPOSITIONS CONTAINING THE SAME

This invention relates to new benzofuranylimidazole derivatives, to a process for their preparation and to pharmaceutical compositions containing them. The imidazole derivatives of this invention have a high selectivity for the imidazoline receptors.

The invention provides benzofuranylimidazole derivatives of the general formula (1)

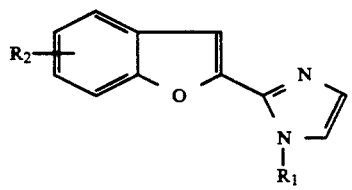

(1)

wherein
$R_1$ represents an hydrogen atom or an alkyl group having from 1 to 6 carbon atoms, and
$R_2$ represents an hydroxy group or $R'_2$ wherein $R'_2$ represents an hydrogen atom, an halogen atom, an alkyl group having from 1 to 6 carbon atoms, or an alkoxy group having from 1 to 5 carbon atoms; and further provides pharmaceutically acceptable salts of such derivatives. Said salts may be those formed with both organic and inorganic acids such as hydrochloric, sulfuric, phosphoric, acetic, citric, propionic, malonic, succinic, fumaric, tartaric, cinnamic, methanesulfonic and p-toluene-sulfonic acids, and preferably hydrochloric acid.

Some series of benzofuranylimidazoline derivatives have been described in the literature. Thus, in Indian J. Chem. 1979, 18B, 254, has been disclosed the following compound

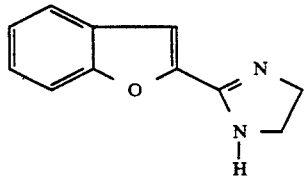

This compound was evaluated for antibacterial and antifungal activity without showing any noteworthy activity. In the U.S. Pat. No. 3,927,023 have been disclosed compounds of the following formula

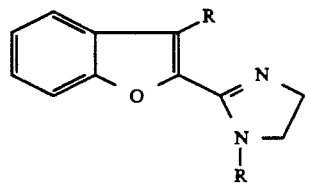

indicated for the treatment of gastric ulcers. Recently, it has been described that some $\alpha_2$-adrenoceptor antagonists also show affinity for the so-called "imidazoline receptor" (see for instance: Laugien et al., Mol. Pharmacol. 1990, 37, 876). The imidazoline receptors are related with the regulation of blood pressure, modulation of insulin release and other biological functions (see for instance: Bousquet et al., Am. J. Med. 1989, (supp 3C), 105). Moreover, it seems that the imidazoline compounds are able to inhibit the noradrenaline release in aorta and pulmonary arteries, involving purinoceptors $P_1$ and prostaglandin receptors (see for instance: Göthert et al., Naunyn-Schmied. Arch. Pharmacol. 1991, 343, 271).

The compounds of the invention possess affinity for imidazoline receptors and very low affinity for the $\alpha_2$-adrenergic receptors.

The invention also provides a process for the preparation of compounds of the general formula (1), the process comprising the two following successive steps:
reacting a compound of the general formula (2)

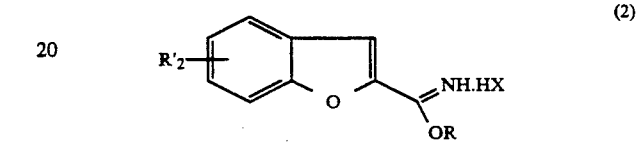

(2)

wherein $R'_2$ is as above defined, R represents an alkyl group having from 1 to 4 carbon atoms and HX represents an acid,
with, at least, one molar equivalent of the aminoacetaldehyde dialkyl acetal, in a polar solvent, for 1 to 24 hours, at a temperature of from $-5°$ C. to the boiling point of the reaction mixture, and
cyclising, in an aqueous acidic medium, for 1 to 24 hours, at a temperature of from 15° to 80° C., the resultant compound of the general formula (3)

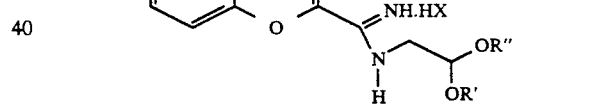

(3)

wherein R' and R" represent, each, an alkyl group having from 1 to 4 carbon atoms, which lead to compounds of the general formula (1) wherein $R_1$ represents an hydrogen atom and $R_2$ represents $R'_2$.

For the preparation of compounds of the general formula (1) wherein $R_1$ represents an alkyl group, the process of the invention comprises the two further steps consisting of the treatment of the compounds of the general formula (1) wherein $R_1$ represents a hydrogen atom, by a base, in an aprotic solvent, at a temperature of from $-10°$ to 25° C., followed by the treatment by the appropriate alkyl-halide or alkyl sulfonate.

For the preparation of compounds of the general formula (1) wherein $R_2$ represents an hydroxy group, the process of the invention comprises a further step consisting of the treatment of the compound of the general formula (1) wherein $R'_2$ represents an alkoxy group, by a dealkylating agent.

In the compounds (2), R preferably represents a methyl or ethyl group and HX preferably represents hydrochloric acid. The aminoacetaldehyde dialkyl acetal with which this compound is reacted is preferably dimethyl- or diethyl-acetal. The reaction is preferably conducted in a polar solvent, such as methanol or ethanol. More preferably, the reaction is conducted for 15-17 hours in refluxing methanol.

In the compounds (3), R' and R" preferably represent a methyl or ethyl group. More preferably, the compounds are heated at 40°-60° C. for 16-20 hours in 10% aqueous hydrochloric acid.

The base used in the conversion of the compounds (1) in which $R_1$ represents an hydrogen atom to the compounds (1) in which $R_1$ represents an alkyl group, is preferably sodium hydride. The reaction may be conducted in an aprotic solvent such as dimethylformamide (DMF), preferably at 0° C.

The dealkylating agent used in the conversion of the compound (1) in which $R_2$ represents an alkoxy group to compounds (1) in which $R_2$ represents an hydroxy group, is preferably selected from within trimethylsilyl iodide and aqueous hydrogen bromide.

The compounds of general formula (2) may be prepared from the corresponding cyano compounds of the general formula (4)

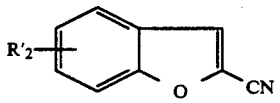

(4)

by treatment with an alcohol of the formula ROH wherein R is as above defined, in the presence of an HX acid. Most conveniently the alcohol used is methanol and HX used is hydrogen chloride.

The cyano compounds (4) may in turn be prepared from the corresponding carboxylic acid of the general formula (5)

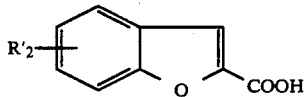

(5)

by treatment with a halogenating agent and subsequent reaction with ammonia, followed by dehydration with phosphorous pentoxide. The acids (5) are obtained according to the method described in J. Am. Chem. Soc. 1951, 73, 872.

Finally, the invention provides a pharmaceutical composition comprising a benzofuranylimidazole derivative of the general formula (1) as above defined or a pharmaceutically acceptable salt of such a derivative in admixture with a pharmaceutically acceptable diluent or carrier.

The following examples illustrate the invention. In these examples, the various compounds and intermediates were characterised by their NMR spectra recorder on a Varian Gemini 200 spectrometer at 200 MHz for $^1H$ and at 50 MHz for $^{13}C$ and are reported in ppm downfield from the resonance of tetramethylsilane. Melting points were measured on a Buchi melting point apparatus in glass capillary tubes and are uncorrected. IR spectra were recorder on a Nicolet 5PC FT-IR spectrophotometer.

EXAMPLE 1

2-(benzofuran-2-yl)imidazole hydrochloride $R_1 = H \quad R_2 = H$ a) preparation of benzofuran-2-carbonyl chloride Thionyl chloride (12.5 ml) was added to a suspension of benzofuran-2-carboxylic acid (20 g) in anhydrous benzene (250 ml). The mixture was refluxed for 3 hours, then allowed to cool down to room temperature. Removal of the volatiles left the desired acid chloride (21.8 g, 98%).

b) preparation of benzofuran-2-carboxamide

Benzofuran-2-carbonyl chloride (21.8 g) was added in small portions to an ice cold solution of ammonia (200 ml, d=0.91). Upon completion of the addition the reaction mixture was allowed to reach room temperature and the desired carboxamide formed a precipitate. The solid was collected by filtration, washed with water and dried in vacuo (17.8 g, 91%). IR: (KBr): 1661 cm$^{-1}$ $^1$H-NMR (DMSO-d$_6$): 7.35 (t,1H), 7.45 (t,1H), 7.60 (s,1H), 7.65 (d,1H), 7.75 (d,1H), 7.70–8.20 (d,2H).

c) preparation of 2-cyanobenzofuran

Phosphorus pentoxide (86 g) was added to a suspension of benzofuran-2-carboxamide (17.8 g) in anhydrous toluene (500 ml) and the mixture was refluxed for 3 hours. After cooling the supernating solution was decanted off and the resulting residue extracted with toluene. The combined toluene fractions were evaporated to leave the cyano compound as an oil (10.7 g, 68%). IR: (NaCl): 2231 cm$^{-1}$ $^1$H-NMR (DMSO-d$_6$): 7.45 (t,1H), 7.55 (t,1H), 7.75 (d,1H), 7.85 (d,1H), 8.10 (s,1H).

d) preparation of methyl benzofuran-2-carboximidate hydrochloride

2-Cyanobenzofuran (10.7 g) was dissolved in ethereal HCl (150 ml, 5M) and methanol (12 ml). The resulting mixture was kept at 4° C. for 48 hours. The resulting solid was filtered, washed with ether and dried (13.4 g, 85%).

$^1$H-NMR (DMSO-d$_6$): 4.30 (s,3H), 7.50 (t,1H), 7.70 (t,1H), 7.80 (d,1H), 7.90 (d,1H), 8.40 (s,1H).

e) preparation of 2-(benzofuran-2-yl)-imidazole hydrochloride

A solution of aminoacetaldehyde dimethylacetal (7.3 g) and methyl benzofuran-2-carboximidate hydrochloride (13.4 g) in methanol (135 ml) was stirred at 60° C. for 16 hours. The mixture was then evaporated to dryness. Hydrochloric acid (750 ml, 2M) was added and the resulting mixture was stirred at 60° C. for 16 hours. After cooling, the solution was washed with dichloromethane. The aqueous layer was basified with sodium hydroxide and the free base was extracted with ethyl acetate. The organic layer was washed with saturated brine and dried. Evaporation of the solvent gave a solid residue which was dissolved in diethyl ether/ethanol. Ethereal HCl was added to solution and the precipitated salt was collected by filtration (12.5 g, 90%).

m.p.=225°–227° C.

$^1$H-NMR (DMSO-d$_6$): 7.40 (t,1H), 7.50 (t,1H), 7.75 (d,1H), 7.85 (s,2H), 7.90 (d,1H), 8.20 (s,1H).

$^{13}$C-NMR (DMSO-d$_6$): 110.4, 112.1, 121.2, 123.4, 124.9, 127.6, 127.8, 135.4, 141.1, 155.1

EXAMPLE 2

1-methyl-2-(benzofuran-2-yl)imidazole hydrochloride $R_1 = CH_3— \quad R_2 = H$

To a solution of the free base (7.0 g) generated from 2-(benzofuran-2-yl)imidazole hydrochloride in DMF (50 ml) at 0° C. was added sodium hydride (1.4 g) 80% in mineral oil in three equal portions. After 30 minutes at room temperature, methyl iodide (2.5 ml) was added dropwise over 15 minutes at 0° C. The mixture was then stirred for 30 minutes at room temperature, poured into water and extracted with ethyl acetate. The organic layer was washed with water and the product was extracted with hydrochloric acid (1M). The aqueous layer was basified with sodium hydroxide and the free base was extracted with ethyl acetate, washed with saturated brine and dried. Evaporation of the solvent gave a solid residue which was dissolved in diethyl ether/ethanol. Ethereal HCl was added to solution and the precipitated salt was collected by filtration (8.1 g, 91%). m.p=232°-235° C.

$^1$H-NMR (DMSO-d$_6$): 4.20 (s,3H), 7.45 (t,1H), 7.55 (t,1H), 7.80 (d,1H), 7.90 (d,1H), 8.00 (d,1H), 8.20 (s,1H).

$^{13}$C-NMR (DMSO-d$_6$): 38.4, 112.0, 112.2, 120.3, 123.3, 125.0, 126.1, 127.2, 128.0, 135.2, 140.2, 155.0.

EXAMPLE 3

2-(6-methoxybenzofuran-2-yl)imidazole hydrochloride

R$_1$=H  R$_2$=6-methoxy

This was prepared from 6-methoxybenzofuran-2-carboxylic acid according to the methods a–e as described in example 1; m.p.=245°-248° C.

$^1$H-NMR (DMSO-d$_6$): 3.90 (s,3H), 7.05 (dd,1H), 7.25 (d,1H), 7.75 (d,1H), 7.80 (s,2H), 8.10 (s,2H).

$^{13}$C-NMR (DMSO-d$_6$): 56.1, 96.2, 110.7, 114.2, 120.6, 120.8, 123.6, 135.6, 140.0, 156.5, 160.4.

EXAMPLE 4

2-(6-hydroxybenzofuran-2-yl)imidazole hydrochloride

R$_1$=H  R$_2$=6-hydroxy

The free base (3.0 g) generated from 2-(6-methoxybenzofuran-2-yl)imidazole hydrochloride was treated with 47% w/v hydrobromic acid solution (30 ml) and the mixture heated at 100° C. for 7 hours with stirring. After cooling the resulting solid was filtered, dissolved in water and basified with sodium bicarbonate. The free base was extracted with ethyl acetate, washed with saturated brine and dried. Evaporation of the solvent gave a solid residue which was dissolved in diethyl ether/ethanol. Ethereal HCl was added to solution and the precipitated salt was collected by filtration (2.2 g, 66%).

$^1$H-NMR (DMSO-d$_6$): 6.95 (dd,1H), 7.10 (d,1H), 7.65 (d,1H), 7.80 (s,2H), 8.00 (s,1H).

$^{13}$C-NMR (DMSO-d$_6$): 97.9, 110.8, 114.8, 119.4, 120.7, 123.6, 135.9, 139.2, 156.7, 158.9.

EXAMPLE 5

1-ethyl-2-(benzofuran-2-yl)imidazole hydrochloride

R$_1$=C$_2$H$_5$—  R$_2$=H

This was prepared from 2-(benzofuran-2-yl)imidazole hydrochloride and ethyl bromide according to the procedure of example 2; m.p.=183°-185° C. $^1$H-NMR (DMSO-d$_6$): 1.55 (t,3H), 4.60 (q,2H), 7.45 (t,1H), 7.55 (t,1H), 7.80 (d,1H), 7.90 (d,1H), 7.95 (d,1H), 8.10 (d,1H), 8.20 (s,1H).

$^{13}$C-NMR (DMSO-d$_6$): 15.4, 44.6, 112.2, 112.2, 121.0, 123.2, 124.4, 124.9, 127.1, 127.9, 134.4, 140.1, 155.1.

EXAMPLE 6

2-(5-bromobenzofuran-2-yl)imidazole hydrochloride

R$_1$=H  R$_2$=5-bromo

This was prepared from 5-bromobenzofuran-2-carboxylic acid according to the methods a–e as described in example 1; m.p.=280° C.

$^1$H-NMR (DMSO-d$_6$): 7.65 (dd,1H), 7.75 (d,1H), 7.85 (s,2H), 8.10 (s,1H), 8.15 (d,1H).

$^{13}$C-NMR (DMSO-d$_6$): 109.3, 114.1, 117.1, 121.6, 125.8, 129.9, 130.3, 135.0, 142.5, 154.0.

EXAMPLE 7

2-(5-methoxybenzofuran-2-yl)imidazole hydrochloride

R$_1$=H  R$_2$=5-methoxy

This was prepared from 5-methoxybenzofuran-2-carboxylic acid according to the methods a–e as described in example 1; m.p.=232°-235° C.

$^1$H-NMR (DMSO-d$_6$): 3.80 (s,3H), 7.10 (dd,1H), 7.40 (d,1H), 7.65 (d,1H), 7.80 (s,2H), 8.10 (s,1H).

$^{13}$C-NMR (DMSO-d$_6$): 56.0, 104.7, 110.3, 112.7, 116.9, 121.2, 128.3, 135.6, 141.8, 150.0, 157.0.

EXAMPLE 8

2-(5-hydroxybenzofuran-2-yl)imidazole hydrochloride

R$_1$=H  R$_2$=5-hydroxy

This was prepared from the free base generated from 2-(5-methoxybenzofuran-2-yl)imidazole hydrochloride according to the procedure of example 4.

$^1$H-NMR (DMSO-d$_6$): 7.00 (dd,1H), 7.15 (d,1H), 7.55 (d,1H), 7.80 (s,2H), 8.00 (s,1H).

$^{13}$C-NMR (DMSO-d$_6$): 106.8, 110.3, 112.4, 117.1, 121.1, 128.4, 135.7, 141.2, 149.4, 155.1.

EXAMPLE 9

1-ethyl-2-(6-methoxybenzofuran-2-yl)imidazole hydrochloride

R$_1$=C$_2$H$_5$—  R$_2$=6-methoxy

This was prepared from 2-(6-methoxybenzofuran-2-yl)imidazole hydrochloride and ethyl bromide according to the procedure of example 2; m.p.=259°-261° C.

$^1$H-NMR (DMSO-d$_6$): 1.50 (t,3H), 3.90 (s,3H), 4.50 (q,2H), 7.15 (dd,1H), 7.35 (d,1H), 7.75 (d,1H), 7.85 (d,1H), 7.95 (d,1H), 8.10 (s,1H).

$^{13}$C-NMR (DMSO-d$_6$): 15.4, 44.4, 56.1, 96.0, 112.2, 114.5, 120.1, 120.5, 123.3, 123.8, 134.5, 138.8, 156.3, 160.2.

The pharmacological activities of the compounds of the invention have been determined according to the following procedures.

Binding studies

Initial biological evaluation of alpha$_1$- and alpha$_2$-adrenoceptor and imidazoline preferring receptor (IR) affinities and selectivities in homogenized rat cerebral cortex were assessed by determining the K$_i$ values of the compounds to displace $^3$H-prazosin $^3$H-clonidine as well as $^3$H-idazoxan in the presence of (—)-adrenaline according to the method of Olmos et al. (J. Neurochem. 1991, 57:1811-1813).

This in vitro model is particularly useful as an initial screening for studying the affinity and the selectivity of these compounds on the imidazoline receptors. The K$_i$ (nM) values of the tested compounds to displace the binding of $^3$H-idazoxan (4 nM) in the presence of (—)-adrenaline (10$^{-6}$M) (IR affinity), $^3$H-clonidine (2 nM) and $^3$H-prazosin (0.5 nM), (alpha$_2$- and alpha$_1$-adrenoceptors affinity respectively), are summarized in table 1; this table shows the potential affinities and selectivities of compounds and two standard drugs regarding these receptors.

Furthermore, the affinities of compounds of the invention for other receptors were also evaluated by determining the $K_i$ values of compounds to displace the binding of $^3$H-pyrilamine (1.1 nM) and $^3$H-tiotidine (11.8 nM) in homogenized guinea-pig cerebral cortex ($H_1$ and $H_2$ histamine receptors, respectively). The $K_i$ values for these compounds resulted to be higher than 10 μM in both subtypes of histamine receptors.

In vivo activity

At present, certain compounds of the invention (Examples 1,2 and 3) have shown an in vivo CNS functional activity, such as: feeding behavior in rats. These compounds induced an acute (1–4 h after the intraperitoneal administration at 25 mg/kg) hyperphagic effect in respect to the control group (7–10-fold, P<0.05), which was lower in potency than those induced by idazoxan (10 mg/kg, i.p.) (cf Table 2: cummulative food intake (g/kg body weight) at 1,2 and 4 hours after intraperitioneal administration of the compounds and the standard drug idazoxan).

However, Example 2 was equally as potent as idazoxan for the $I_2$-imidazoline receptors according to the data derived from binding studies but much more selective (cf Table 1). Also, the selectivity ratio for IR/alpha$_2$ and IR/alpha$_1$ are indicated.

Thus, these compounds may have a therapeutic as appetite stimulants and/or antianorexics. Other data obtained in different laboratories also support the therapeutic potential of imidazoline drugs acting upon imidazoline receptors as appetite stimulants and/or antianorexics (Jackson et al., Br. J. Pharmacol. 1991, 104, 258–262).

The compounds of the invention have been found deprived of action on serotonin receptors.

On the other hand, an approximative LD$_{50}$ was obtained from the Irwin test performed in mice (4 animals, 50% males and females), where compounds of the invention (all at 100 mg/kg, i.p.) did not cause any death during 72 hours. So, the approximative intraperitoneal LD$_{50}$ in mice for these compounds was higher than 100 mg/kg.

In accordance to their physical, chemical and pharmaceutical characteristics, these compounds may be prepared in a form suitable for oral, rectal or parenteral administration. Such oral compositions may be in the form of capsules, tablets, granules or liquid preparations such as elixirs, syrups or suspensions.

Tablets contain a compound or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatin, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or kaolin in a hard gelatin capsule.

Compositions for parenteral administration may be in the form of sterile injectable preparations such as solutions or suspensions, for example: water or saline.

For the purposes of convenience and accuracy, the compositions are advantageously employed in a unit dosage form. For oral administration the unit dosage form contains from 0.5 to 300 mg, preferably 1 to 100 mg of the compounds or a non-toxic salt thereof. Parenteral unit dosage forms contain from 0.05 to 20 mg of the compounds or a non-toxic salt thereof per 1 mL of the preparation.

TABLE 1

| Compound | Affinity ($K_i$, nM) | | | Selectivity | |
|---|---|---|---|---|---|
| | IR | Alpha$_2$ | Alpha$_1$ | IR/α$_2$ | IR/α$_1$ |
| Example 1 | 89 | 100 148 | 36 540 | 1 125 | 410 |
| Example 2 | 15 | 62 061 | 26 169 | 4 137 | 1 744 |
| Example 3 | 151 | 56 150 | 17 800 | 372 | 118 |
| Example 5 | 117 | 68 350 | 33 258 | 584 | 284 |
| Example 7 | 163 | 98 719 | 4 405 | 605 | 27 |
| Example 9 | 123 | 71 320 | 22 615 | 580 | 184 |
| Idazoxan | 14 | 5 | 91 | 0.4 | 6.5 |
| RX 821002 | 44 902 | 0.7 | ND | 0.00002 | — |

The results are the mean of 10 experiments. RX 821002 is the methoxy derivative of idazoxan.
ND: not determined

TABLE 2

| Compounds | Dose mg/kg | N | Time (h) | | |
|---|---|---|---|---|---|
| | | | 1 | 2 | 4 |
| Carboxymethylcellulose 0.5% | — | 5 | 0.04 ± 0.01 | 0.2 ± .05 | 0.6 ± 0.1 |
| Idazoxan | 10 | 5 | 3.7 ± 1.2** | 5.6 ± 2.1** | 7.4 ± 2.3** |
| Example 1 | 25 | 5 | 3.0 ± 2.0** | 4.0 ± 2.1** | 4.8 ± 2.0** |
| Example 2 | 25 | 5 | 2.7 ± 1.5** | 3.0 ± 1.5 | 3.6 ± 1.4* |
| Example 3 | 25 | 5 | 1.3 ± 1.0* | 3.4 ± 1.2* | 3.8 ± 1.2* |

*significant
**highly significant

I claim:
1. Process for the preparation of benzofuranylimidazole derivatives of the formula (1)

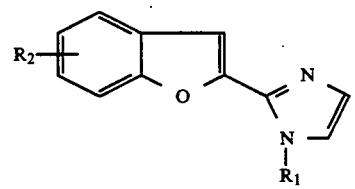

(1)

wherein
R$_1$ represents a hydrogen atom, and
R$_2$ represents a hydrogen atom, a halogen atom, an alkyl group having from 1 to 6 carbon atoms or an alkoxy group having from 1 to 5 carbon atoms;
or a therapeutically acceptable salt of such a derivative, the process comprising the following successive steps:
reacting a compound of formula (2)

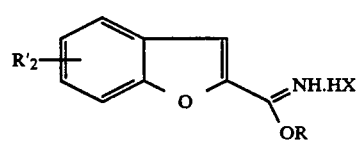

(2)

wherein R represents an alkyl group having from 1 to 4 carbon atoms and HX represents an acid, with, at least, one molar equivalent of an aminoacetaldehyde dialkyl acetal, in a polar solvent, for 1 to 24 hours, at a temperature of from −5° C. to the boiling point of the reaction mixture thereby obtaining a compound of the formula (3)

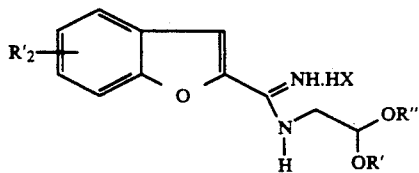
(3)

wherein R' and R" represent, each, an alkyl group having from 1 to 4 carbon atoms, and cyclizing, in an aqueous acidic medium, for 1 to 24 hours, at a temperature of from 15° to 80° C., the compound of the formula (3), said cyclizing resulting in compounds of the formula (1).

2. The process of claim 1 further including the process of substituting on the compound of the formula (1) a selected alkyl group having from 1 to 6 carbon atoms for the $R_1$ hydrogen, said process comprising the steps of treatment of the compound of the formula (1) by a base, in an aprotic solvent, at a temperature of from $-10°$ C. to 25° C., followed by treatment with an alkyl halide or alkyl sulfonate, said alkyl halide or alkyl sulfonate having the said selected alkyl group.

3. The process of claim 1 further including the process of substituting on the compound of the formula (1) a hydroxy group at $R_2$, the process comprising selecting a compound according to formula (1) wherein $R_2$ is alkoxy, and treating said compound with a dealkylating agent selected from the group consisting of trimethylsilyl iodide and aqueous hydrogen bromide.

4. Process according to claim 1 wherein the first step is conducted for 15-17 hours in refluxing methanol.

5. Process according to claim 1 wherein the second step is conducted at 40°-60° C. for 16-20 hours in 10% aqueous hydrochloric acid.

6. Process according to claim 2 wherein the first step is conducted with sodium hydride, in dimethylformamide at 0° C.

* * * * *